United States Patent [19]

Ysebaert

[11] Patent Number: 4,994,043

[45] Date of Patent: Feb. 19, 1991

[54] TWO COMPARTMENT SYRINGE

[75] Inventor: Willem M. Ysebaert, Hendriklaan, Netherlands

[73] Assignee: Akzo N.V., Arnhem, Netherlands

[21] Appl. No.: 207,082

[22] Filed: Jun. 15, 1988

[30] Foreign Application Priority Data

Jun. 16, 1987 [EP] European Pat. Off. .......... 87.201141

[51] Int. Cl.⁵ ...................... A61M 5/00; A61M 37/00
[52] U.S. Cl. ...................................... 604/191; 604/90
[58] Field of Search ...................... 604/89–92, 604/82, 191, 218, 56, 211

[56] References Cited

U.S. PATENT DOCUMENTS

| | | | |
|---|---|---|---|
| 2,549,417 | 4/1951 | Brown | 604/90 |
| 2,607,344 | 8/1952 | Brown | 604/125 |
| 3,052,240 | 1/1959 | Silver et al. | 604/89 |
| 3,108,591 | 10/1963 | Kolbas | 604/89 |
| 3,477,431 | 11/1969 | Walecka | 604/89 |
| 3,494,359 | 2/1970 | Zackheim | 604/90 |
| 3,914,419 | 10/1975 | Haeger et al. | 424/237 |
| 4,065,360 | 12/1977 | Kreb, III | 604/82 |
| 4,226,236 | 10/1980 | Genese | 604/89 |
| 4,599,082 | 7/1986 | Grimard | 604/90 |
| 4,613,326 | 9/1986 | Szwarc | 604/238 |
| 4,792,329 | 12/1988 | Schreuder | 604/90 |
| 4,818,517 | 4/1989 | Kwee et al. | 604/36 |

FOREIGN PATENT DOCUMENTS

| | | | |
|---|---|---|---|
| 730362 | 1/1943 | Fed. Rep. of Germany . | |
| 2191912 | 2/1974 | France | 604/82 |
| 1214053 | 12/1970 | United Kingdom | 604/82 |
| 1306126 | 2/1973 | United Kingdom . | |
| 0244228 | 5/1969 | U.S.S.R. | 604/82 |

Primary Examiner—C. Fred Rosenbaum
Assistant Examiner—Sharon Rose
Attorney, Agent, or Firm—William M. Blackstone

[57] ABSTRACT

Disclosed is a two compartment syringe having at least two by-passes which selectively allow an easy flow from one compartment to the other compartment.

The liquid (injection fluid) is in the "needle" compartment and the solid medicament is in the "plunger" compartment. Associated with the plunger compartment is an aperture or other means for allowing the escape of fluids from that compartment during a lyophilization process.

14 Claims, 2 Drawing Sheets

TWO COMPARTMENT SYRINGE

BACKGROUND OF THE INVENTION

1. Field of the Invention

The present invention is directed to a two compartment syringe and more particularly to a two compartment syringe provided with a so-called by-pass.

2State of the Art

Injectable medicaments often show a rapid loss of potency when they are in their ready to use form.

A solution of this problem is found in applying a two compartment syringe system, one compartment containing the solid medication (either in powder form or preferably in lyophilized form) and the other compartment containing the injection fluid. The oldest two compartment system usually consists of two vials with pierceable stoppers. However, this two vials system commonly presents problems with respect to sterility since only the interior of the vials are sterile and bacteria from the exterior of the vials may easily be introduced into the medication during the mixing procedure.

The two compartment syringes as described in U.S. Pat. No. 2,607,344 and South African Pat. No. 84 04 195 therefore embody a major improvement over the two vial system.

The above-mentioned South African patent more particularly discloses a two compartment medication syringe that comprises:

1. a barrel having a chamber for retaining medication;
2. a tip extending from a distal end of said barrel having a passageway therethrough communicating with said chamber, said tip including means for accepting a hypodermic needle;
3. a by-pass stopper slidably positioned in fluid-tight engagement inside said barrel;
4. A raised peripheral portion of said barrel serving as a by-pass and defining a by-pass zone, said by-pass zone being longer along the longitudinal axis of said barrel than the length of said by-pass stopper along the longitudinal axis of said barrel, said by-pass positioned so that when said by-pass stopper is within said by-pass zone, the volume defined within said chamber between said by-pass stopper and said distal end of said barrel is approximately the volume of the combined components of the medication, said by-pass being raised enough to allow fluid flow around said by-pass stopper when said by-pass stopper is positioned within said by-pass zone; and a stopper slidably positioned in fluid-tight engagement inside said barrel adapted to engage a plunger rod to facilitate its operation, said stopper capable of moving fluid from said chamber through said passageway upon its movement toward said distal end.

This syringe minimizes sterility problems by allowing the mixing and administering steps to be performed without puncturing stoppers or transferring the medication compounds through surfaces which are exterior to the syringe assembly.

The medication syringe according to the South African patent has a compartment defined by the tip and the by-pass stopper, and a second compartment defined by the by-pass stopper and the stopper adapted to engage the plunger rod. Hereinafter compartment A will be called the "needle-compartment" and compartment B the "plunger-compartment" indicating the relative position of the compartments in the barrel.

The needle compartment of the syringe according to the South African patent is intended to contain the solid lyophilized medicament and consequently the plunger compartment is filled up with the injection fluid. This syringe is, indeed, very suitable because lyophilization of the medicament can be carried out directly in the needle compartment itself.

The medication syringe according to the South African patent is, however, less suitable or even unsuitable for use if the injection fluid is to be stored in the needle compartment and the solid or lyophilized medicament in the plunger compartment, because efficient mixing of the two components is impossible.

Under certain circumstances it is easier from a manufacturing point of view or even desired to fill the needle compartment with the injection fluid and to sterilize the syringe and then afterwards to add the medication either in powder or in lyophilized form aseptically into the plunger compartment.

SUMMARY OF THE INVENTION

The present invention provides a medication syringe of the type as disclosed in the South African patent but especially suitable for use where the injection fluid is to be stored in the needle compartment and the medicament in powder of lyophilized form in the plunger compartment.

The two compartment syringe according to the invention comprises:

(1) a barrel;
(2) a tip extending from a distal end of said barrel having a passageway therethrough connecting the interior of the barrel with the outside, said tip including means for accepting a hypodermic needle;
(3) a by-pass stopper slidably positioned in fluid-tight engagement inside said barrel thus forming a compartment "a" between the tip and by-pass stopper;
(4) at least two raised peripheral portions of said barrel serving as by-passes and defining possibly distinct by-pass zones, said by-pass zones each being longer along the longitudinal axis of the barrel than the length of said by-pass stopper (measured along the longitudinal axis of said barrel). Said by-passes positioned so that when said by-pass stopper is moved in the direction of the said tip it comes within each by-pass zone simultaneously and then defines a volume of compartment "a", that is at least the volume of the combined medication components, said by-passes being raised enough to allow a fluid flow around the by-pass stopper when said by-pass stopper is positioned within the by-pass zones; and (5) a stopper slidably positioned in fluid-tight engagement inside the barrel and adapted to engage a plunger rod, thus forming a compartment "b" between said stopper and said by-pass stopper.

In accordance with a preferred embodiment of the present invention the two compartment syringe includes an elongate substantially cylindrical barrel, and includes sealing means releaseably connected to the tip in order to close the passageway. Also provided are two raised peripheral portions of said barrel serving as by-passes and defining one by-pass zone, said two by-passes being positioned at approximately opposite sites of the barrel. The preferred embodiment further includes a liquid component (the injection fluid) being contained within compartment "a" and the solid medicament either in powder or in lyophilized form being contained in compartment "b".

A further improvement of the above preferred syringe according to the invention renders it possible to lyophilize a solution of a medicament in the interior of compartment "b" in a very simple manner.

For that purpose compartment "b" of the syringe of the invention is provided with a small opening in the wall, a bypass or other means which provides an open connection with the outside.

The syringe containing the injection fluid in compartment "a" and a solution of the medicament in a compartment "b" (that is provided with the previously mentioned open connection with the outside) is placed in a lyophilizer and lyophilized whereby the solvent in compartment "b" is allowed to escape through the opening, bypass or the like.

After the termination of the lyophilization process compartment "b" is closed by simply moving the stopper (adapted to engage a plunger rod) in such a manner that it completely closes the connection with the outside resulting in a sealed compartment "b" containing the lyophilized residue.

DESCRIPTION OF THE PREFERRED EMBODIMENTS

The syringe according to the invention will now be described more in detail with a reference to FIGS. 1 and 2.

Figure 1:
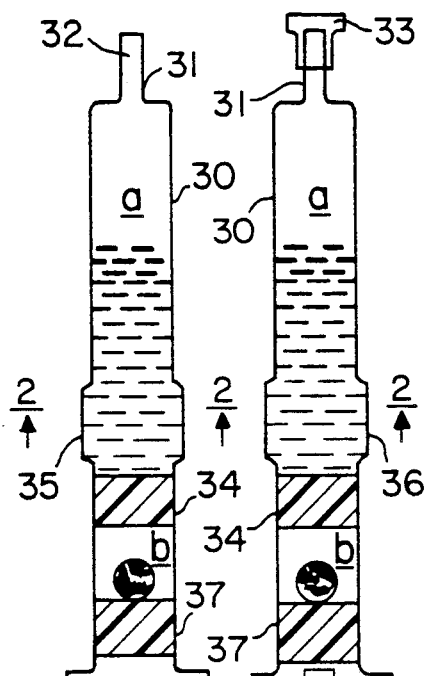
FIG. 1 is a cross-sectional view of the syringe according to the invention.
Figure 2:
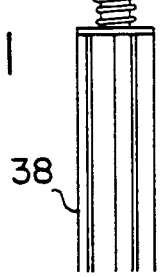
FIG. 2 shows the same syringe as in FIG. 1 including the plunger rod and tip cap.

The two compartment syringe of FIG. 1 includes an elongate substantially cylindrical barrel 30 with the tip 31 extending from a distal end of the barrel 30 and having a passageway 32 communicating with the outside. Tip cap 33 is releaseably connected to tip 31 and seals passageway 32 in an air-tight manner. A flexible by-pass stopper 34 is slidably positioned in fluid tight arrangement inside the barrel thus forming a compartment "a" between tip 31 and by-pass stopper 34.

Figure 3:
FIG. 3 is an enlarged cross-sectional view of the syringe of FIG. 1 taken along line 2—2 with the by-pass stopper in the by-pass zone.

The syringe barrel also includes tow by-passes 35 and 36 defining in this embodiment one by-pass zone along the barrel. Both by-passes are large enough to allow fluid flow around the by-pass stopper when the by-pass stopper is positioned within the by-pass zone. The by-passes as shown in FIG. 3 effectively enlarges the inside diameter of the barrel within the by-pass zone.

A flexible stopper 37 is slidably positioned in fluid tight engagement inside the barrel thus forming a compartment "b" between stopper 37 and by-pass stopper 34. Stopper 37 is furthermore adapted to engage plunger rod 38 preferably provided with rod flange 39 (see FIG. 4) as a convenient structure for applying forces to move the plunger rod.

The preferred embodiment of the instant invention contains two components of the medication which will be mixed at the time of use. A liquid, usually the injection fluid, is contained within the compartment "a" and a medicament in powder-or lyophilized form in compartment "b".

Figure 5:
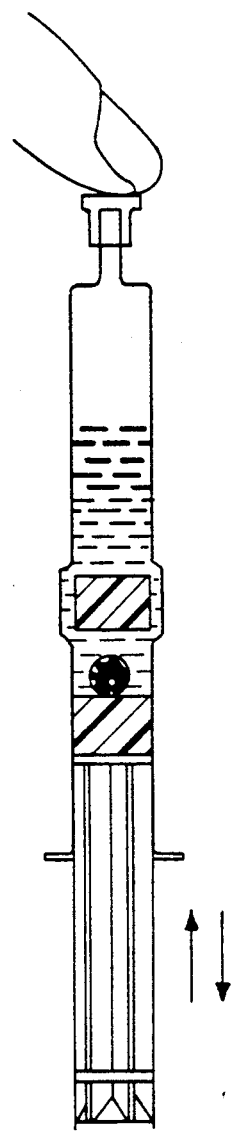
FIG. 5 schematically shows the further mixing of the components started in FIG. 4 by gently moving the piston up and down to completely dissolve the solid or lyophilised medicament, whereby the tip must be kept tightly closed.
Figure 4:
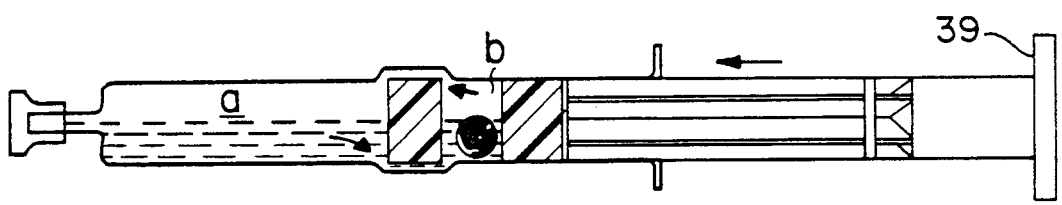
FIG. 4 has the by-pass stopper within the by-pass zone and schematically shows the mixing of the medication components with closed tip, the lower by-pass allowing fluid flow from compartment "a" to compartment "b" and the upper by-pass allowing air flow from "b" to "a".
Figure 6:
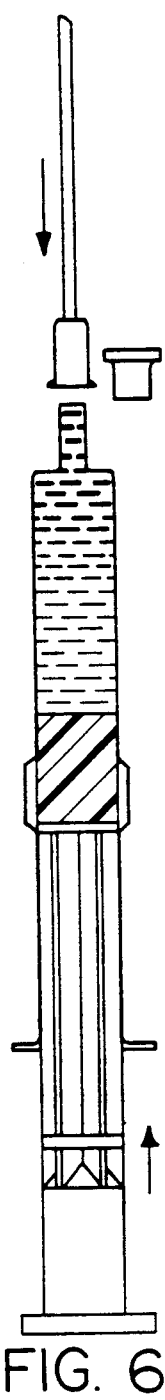
FIG. 6 is a side elevation (and cross-sectional) view of the syringe which after attachment of the needle is ready for use.

The FIGS. 4 and 5 clearly show the best way of handling in order to mix the medication components. This handling can be carried out while the passageway 32 is being kept sealed.

Figures 7, 8:
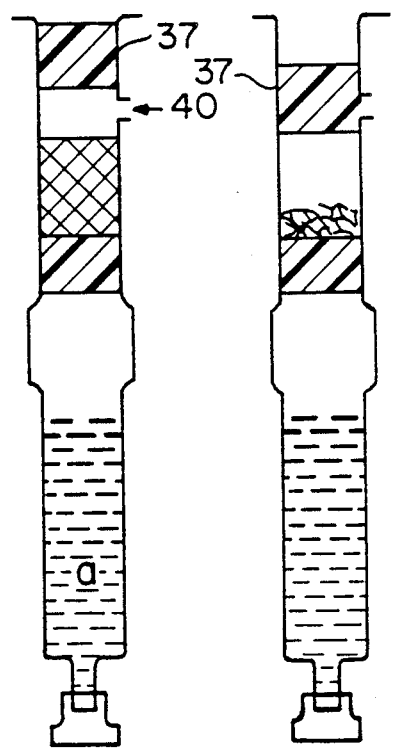
FIG. 7 illustrates a syringe according to the invention which is ready for lyophilising a solution of the medicament in compartment "b"
FIG. 8 shows the syringe of FIG. 7 after the lyophilising process.

FIG. 7 shows a syringe of invention, in which compartment "b" is provided with an opening 40. This opening (which also can be any other means that provides an open connection with the outside, such as a bypass) allows for easy lyophilization of a solution of the medicament in compartment "b".

FIG. 8 illustrates the syringe of FIG. 7 after the lyophilizing process whereby opening 40 is now closed by the stopper 37.

The syringe barrel may be constructed of thermoplastic material or glass, while the stopper, by-pass stopper and tip cap may be made of a wide variety of materials such as natural and synthetic rubbers. Obviously the materials used must be compatible with the medication to be stored.

The syringe according to the present invention includes advantages over the prior art syringe in that
  for a given volume of powder and solution, the required volume of the syringe can be much smaller (25–40%) hence this syringe is cheaper and easier to handle by the doctor and
  in pharmaceutical processing it is now possible to fill the (cheap) injection fluid and afterwards (after quality control) to add the (expensive) solid medicament.
  with a simple modification (opening in the wall of compartment "b") of the syringe it is moreover possible to carry out the lyophilizing process in the interior of compartment "b".

I claim:

1. A two compartment syringe for containing and combining separated medication components comprising
  a barrel;
  a tip extending from a distal end of said barrel having a passageway therethrough connecting the interior of the barrel with the outside;
  a by-pass stopper slidably positioned in fluid-tight engagement inside said barrel thus forming a first compartment between said tip and said by-pass stopper;
  at least two raised peripheral portions of said barrel serving as by-passes and defining by-pass zones, said by-pass zones each being longer than the length of said by-pass stopper measured along the longitudinal axis of said barrel, said by-passes positioned so that when said by-pass stopper is moved in the direction of the tip it comes within each by-pass zone simultaneously, said by-passes being raised enough to allow fluid flow around the by-pass stopper when said by-pass stopper is positioned within the by-pass zones; and a stopper slidably positioned in fluid-tight engagement inside said barrel and adapted to engage a plunger rod, thus forming a second compartment between said stopper and said by-pass stopper, said second compartment having means separate from said tip passageway for allowing the escape of a fluid therefrom during a lyophilization process, said means comprising a small opening in the wall of the barrel associated with the second compartment, which means can be closed by moving the stopper in the direction of the tip.

2. The syringe of claim 1 wherein said barrel is elongate and substantially cylindrical and further including means for sealing said passageway releaseably connected to the tip.

3. The syringe of claim 2 having two by-passes defining one by-pass zone along the barrel, said by-passes being positioned at approximately opposite sides of the barrel.

4. The syringe of claims 1, 2 or 3 wherein a liquid is contained in the compartment "a" and a solid medicament in the compartment "b".

5. The syringe of claim 4 wherein the solid medicament is lyophilized.

6. The syringe of claim 1 wherein said means for allowing the escape of solvent from the second compartment is a by-pass for providing an open connection exterior to the syringe.

7. The syringe of claim 1 wherein said tip includes means for accepting a hypodermic needle.

8. The syringe of claim 1 wherein the by-passes define distinct by-pass zones.

9. The syringe of claim 1 wherein the first compartment is at least the volume of the combined medication components.

10. A multi-compartmented syringe for containing and combining a liquid medication component and a dry medication component comprising:

a barrel, said barrel being elongate and substantially cylindrical;

a tip extending from a distal end of the barrel, the tip having a passageway therethrough connecting the barrel's interior with the barrel's exterior;

a by-pass stopper slidably positioned in fluid-tight engagement within the barrel forming, in conjunction with the interior wall of the barrel associated therewith, a first compartment for containing the liquid medication component between the tip and the by-pass stopper;

two by-passes, said by-passes being raised peripheral portions of the barrel and defining by-pass zones, each by-pass zone having a length longer along the longitudional axis of the barrel than the length of the by-pass stopper along the longitudinal axis of the barrel, said by-passes positioned so that when said by-pass stopper is moved longitudinally in the direction of the tip, the by-pass stopper enters each by-pass zone simultaneously, said by-passes further being sufficiently large to allow fluid flow around the by-pass stopper when said by-pass stopper is positioned within the by-pass zones; and a stopper slidably positioned in fluid-tight engagement inside a proximal end of the barrel and adapted to engage a plunger rod, said stopper forming, in conjunction with the wall of the barrel associated therewith and the by-pass stopper, a second compartment for containing the dry medication component between the stopper and the by-pass stopper, said second compartment having aperture means associated therewith for allowing the escape of evaporated solvent through during a lyophilization process, which aperture means can be closed by moving the stopper in the direction of the tip without discharging one of the medication components or both through the passageway.

11. The syringe of claim 10 wherein said tip includes means for accepting a hypodermic needle.

12. The syringe of claim 11 wherein said aperture means is a hole formed in the wall of the barrel associated the second compartment.

13. The syringe of claim 11 wherein the by-passes define distinct by-pass zones.

14. The syringe of claim 10 wherein the volume of the first compartment is greater than or equal to the volume of the combined medication components.

* * * * *